United States Patent
Casperson et al.

(10) Patent No.: US 6,764,523 B2
(45) Date of Patent: Jul. 20, 2004

(54) TWO-PART AQUEOUS COMPOSITION FOR OXIDATIVE COLORATION OF HAIR

(75) Inventors: Stephen Casperson, Milford, CT (US); Zubaida Khan, Stamford, CT (US); Kue-Yick Lee, Stamford, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 214 days.

(21) Appl. No.: 10/160,649

(22) Filed: Jun. 3, 2002

(65) Prior Publication Data

US 2002/0194683 A1 Dec. 26, 2002

Related U.S. Application Data

(63) Continuation-in-part of application No. 09/855,301, filed on May 15, 2001, now abandoned.

(51) Int. Cl.⁷ .................................................. A61K 7/13
(52) U.S. Cl. ..................... 8/405; 8/406; 8/410; 8/421; 8/552; 8/111
(58) Field of Search ........................... 8/405, 406, 410, 8/421, 552, 111

(56) References Cited

U.S. PATENT DOCUMENTS

| | | | |
|---|---|---|---|
| 3,303,213 A | 2/1967 | Kalopissis et al. | 260/534 |
| 3,331,781 A | 7/1967 | Kalopissis et al. | 252/152 |
| 3,436,167 A | 4/1969 | Kalopissis et al. | 8/10.1 |
| 3,891,385 A | 6/1975 | Kalopissis et al. | 8/10.1 |
| 3,986,825 A | 10/1976 | Sokol | 8/10.1 |
| 4,240,450 A | 12/1980 | Grollier et al. | 132/7 |
| 4,362,528 A | 12/1982 | Grollier et al. | 8/406 |
| 4,402,700 A | 9/1983 | Feinland et al. | 8/416 |
| 4,532,127 A | 7/1985 | Feinland et al. | 424/62 |
| 4,563,188 A | 1/1986 | Bugaut et al. | 8/410 |
| 4,663,158 A | 5/1987 | Wolfram et al. | 424/70 |
| 4,772,462 A | 9/1988 | Boothe et al. | 424/70 |
| RE33,786 E | 1/1992 | Pohl et al. | 8/406 |
| 5,137,538 A | 8/1992 | Madrange et al. | 8/410 |
| 5,376,146 A | 12/1994 | Casperson et al. | 8/408 |
| 5,393,305 A | 2/1995 | Cohen et al. | 8/406 |
| 5,752,983 A * | 5/1998 | Audousset et al. | 8/409 |
| 5,976,195 A | 11/1999 | de la Mettrie et al. | 8/411 |
| 6,074,439 A | 6/2000 | De La Mettrie et al. | 8/411 |
| 2002/0041855 A1 | 4/2002 | Glenn, Jr. | 424/70.1 |

* cited by examiner

*Primary Examiner*—Brian P. Mruk
*Assistant Examiner*—Eisa Elhilo
(74) *Attorney, Agent, or Firm*—Brian M. Bolam; Tara M. Rosnell

(57) ABSTRACT

A two-part high aqueous-content system for oxidative coloration of hair utilizing an aqueous dye lotion formulation containing hydroxypropyl bisisostearamidopropyldimonium chloride conditioner, optionally with one or more surfactants.

29 Claims, No Drawings

TWO-PART AQUEOUS COMPOSITION FOR OXIDATIVE COLORATION OF HAIR

RELATED APPLICATION

This application is a continuation-in-part of U.S. Pat. application Ser. No. 09/855,301, filed May 15, 2001 abandoned.

FIELD OF THE INVENTION

This invention relates to high aqueous-content hair coloring compositions with good thickening and conditioning properties without detrimental effects on the hair dyeing properties of the composition.

BACKGROUND TO THE INVENTION

When oxidation dyes of the type comprising primary intermediates and couplers are used in the dyeing of human hair, the procedure usually involves the use of a two-part system. One part is a dye lotion formulation that contains a variety of ingredients, including at least one of the oxidation dye precursors. The other part is a developer composition that contains a suitable oxidizing agent such as hydrogen peroxide, which, as a consequence of its bleaching effect, may remove some of the natural melanin pigment of the hair by oxidizing it. To dye hair, the dye lotion and the developer composition are admixed at the time of use. When the dye lotion and the developer composition are mixed immediately prior to application to the human hair, the composite composition preferably exhibits an increase in its viscosity so that the composite composition stays on the hair and does not drip onto the face and down the neck of the consumer. The precursors in the dye lotion penetrate into the hair and are oxidized to produce the desired color. Such systems will generally contain 50% or more of organic solvents and surfactants, and require relatively high levels of dye precursors to produce the desired color.

Several conditions are important for the procedures using oxidative dyes to work properly. These include the following:

1. The formulations must be stable to insure a reasonable shelf life.
2. The compositions formed by mixing the dye lotion and developer must have rheological properties whereby application, either by use of a brush or with the fingers, can readily distribute the dye composition throughout the hair mass, which in the absence of sheer, does not drip or run from the hair during the color development period.
3. The dye mixture, as applied to the hair, should allow rapid diffusion of the dye precursors from the dye mixture into the hair fiber.
4. The mixture, while thick enough to stay in place during the color development period, should be readily rinseable from the hair with water.
5. The mixture should preferably contain conditioning agents that leave the hair in a condition such that it is easy to detangle while wet and also feel smooth and be readily managed when dry.
6. The dye lotion and developer should preferably, but not necessarily, have comparable viscosities in order to facilitate mixing.
7. The dyeing effect should be rapid, with a dyeing time preferably under thirty minutes.

In conventional permanent hair dye products, the rheological properties can be attained by the use of a dye lotion containing a high level of surfactants and organic solvents to provide a thin lotion, which, on mixture with a highly aqueous developer solution of the oxidizing agent, form a dye mixture with the desired gel-like consistency. The preferred surfactants in commercial products are nonionic or anionic materials, which do not provide any conditioning. The preferred conditioners for human hair are cationic surfactants, e.g., monomeric quaternary ammonium compounds, and cationic polymers that provide excellent conditioning, but are incompatible with anionic surfactants.

There have been many efforts to produce oxidative hair dyeing compositions having the desired properties, listed above.

U.S. Pat. Nos. 3,303,213; 3,331,781; 3,436,167 and 3,891,385 describe the use, in hair treating compositions, of specific amphoteric surfactants such as the sodium salt of $N-(N^1,N^1$-dimethyl-aminopropyl)-$N^2$-alkyl (fatty) asparagine wherein the "fatty" moiety is derived from the fatty acids of tallow. According to the patents, the amphoteric surfactant can be employed with organic solvents and any of a variety of cationic, anionic or non-ionic surface active agents. There is no indication of the use of quaternary ammonium salts in the compositions.

U.S. Pat. No. 4,402,700 describes hair dyeing compositions containing quaternary ammonium compounds and also cites the possible uses of amphoteric surfactants in the compositions. These compositions, however, require the uses of organic solvents and nonionic surfactants, and the amount of water in the compositions is less than 50%.

U.S. Pat. No. 4,532,127 describes hair coloring compositions containing oxidative dyes together with an oxidizing agent. The compositions require the presence of quaternary amine compounds containing two long chain alkyl radicals each having about 10 to 26 carbon atoms. Any of a variety of surfactants may be present in the composition that, although they have a high water content, may contain organic solvents. The dye lotions of the patent contain di-long chain alkyl quaternary ammonium compounds in the presence of relatively large amounts of non-ionic surfactants. They are said to be superior to a comparison lotion containing a mono-long chain alkyl quaternary ammonium compound in combination with an amphoteric surfactant. The lotions of this patent suffer from the disadvantage of having high levels of surfactant thus inhibiting rapid diffusion of the dye precursors into the hair. Furthermore, di-long chain alkyl quaternary ammonium compounds are poorly biodegradable, particularly as compared to the mono-long chain alkyl quaternary ammonium compounds. The compositions disclosed are free of anionic surfactants and anionic polymers.

U.S. Pat. No. 4,663,158 describes hair conditioning compositions containing an amphoteric surfactant together with at least one quaternary cationic polymer such as poly (methacrylamidopropyl)trimethyl ammonium chloride. The compositions are acidic.

U.S. Pat. No. 4,563,188 discloses hair dyeing compositions containing specific para-phenylenediamine derivatives, which may contain any of several types of surfactants as well as organic solvents.

U.S. Pat. No. 5,137,538 describes oxidative hair dyeing compositions containing specific para phenylenediamines and $N,N^1$-diphenylalkylenediamines. The compositions may be acidic or alkaline. They may contain organic solvents and anionic, cationic, non-ionic or amphoteric surfactants.

U.S. Pat. No. 4,362,528 refers to compositions said to be useful for hair coloring. These compositions comprise oxidative dyes together with any of a variety of cationic polymers. The hair is first treated with such composition and subsequently rinsed with a shampoo composition containing an anionic detergent.

U.S. Pat. No. 4,240,450 describes hair treating mixtures such as shampoos and hair coloring compositions, which may be oxidative. The compositions include cationic and anionic polymers that may be chosen from hundreds of such polymers, which are generically and specifically described.

U.S. Pat. No. 3,986,825 refers to a variety of hair coloring composition which may be employed with either oxidizing agents or reducing agents and which employ any of a wide variety of surfactant water soluble polymer additives together with anionic, cationic, nonionic or amphoteric surfactants.

U.S. Pat. No. Re. 33786 teaches that rapid dyeing with highly aqueous compositions can be achieved through the use of a certain acrylate copolymer viz an acrylate/steareth-20 methacrylate copolymer in the developer. A similar system employing a certain anionic copolymer of acrylic acid or methacrylic acid with their lower alkyl esters is disclosed in U.S. Pat. No. 5,393,305. Also, in U.S. Pat. No. 5,376,146 the use of a combination of anionic acrylic polymers, such as the copolymers of both RE 33786 and U.S. Pat. No. 5,393,305, is disclosed. In U.S. Pat. No. 5,976,195 and U.S. Pat. No. 6,074,439 the use of anionic polymers containing at least one allyl ether unit is taught to improve gelling properties of such hair coloring compositions. Such polymers produce a thickening effect only when the developer is added to the alkaline lotion containing the color precursor. The disadvantage of the use of acrylate copolymers, or any other anionic polymer, as used in these patents is that they tend to deactivate quaternary ammonium conditioning compounds by complexation.

SUMMARY OF THE INVENTION

It is an object of this invention to provide stable hair dyeing compositions which avoid the aforesaid problems while at the same time providing high aqueous content, acceptable rheological profile, rapid dyeing permanent hair coloring systems having a minimized drying effect and improved storage properties, and exhibiting excellent conditioning properties. A further object of this invention is to produce such composition employing lowered levels of surfactant in the dyeing composition.

It is a further object of the invention to provide lotion and developer formulations which can be readily formed into a thickened mixture, preferably a gel, having an appropriate viscosity to remain on the hair for a sufficient period to achieve the desired hair coloring effect while still providing good conditioning characteristics.

It is yet another object of this invention to provide hair coloring compositions that provide enhanced conditioning benefits for the hair dyeing compositions, while decreasing the overall amount of conditioning agent employed in the compositions.

It is a still further object of this invention to a provide hair coloring composition which also impart a durable, more efficient coloring effect while maintaining a good conditioning effect to treated hair and which adds thickening benefits, particularly when employing monomeric quaternary compounds.

A further object of this invention is to provide a hair coloring composition, which provides excellent wet feel and wet combing characteristics immediately after the dyeing mixture is washed from the hair.

The invention comprises a hair dyeing composition containing hydroxypropyl bisisostearamidopropyldimonium chloride (also referred to herein as HPBISAPDC) as the primary conditioning material in a two-part aqueous hair dyeing composition. HPBISAPDC is available as Schercoquat 21AP sold by Scher Chemicals, Inc. of Clifton, N.J., which contains 85% HPBISAPDC in a 15% propylene glycol diluent. The invention also comprises a two-part hair aqueous dyeing composition comprising a dye lotion formulation containing oxidizable dye precursors; at least about 50% by weight water, and a conditioning effective amount of HPBISAPDC conditioning agent.

This invention comprises a two-part system comprising aqueous, oxidative, hair coloring compositions (lotions and developers) for mixture with each other shortly before use. The lotion comprises an aqueous alkaline composition having a pH of from about 7 to 11 and a water content of at least about 50% by weight, a tinctorily effective amount of oxidative dye precursors, and a hair conditioning effective amount of HPBISAPDC conditioning agent. The second part, i.e., the developer, is an aqueous composition with a pH of from about 2 to about 6, preferably 2 to 3, containing a peroxide oxidizing agent.

The invention also comprises a kit or package of the developer and dye lotion formulations. A further aspect of this invention is the use of such two-part systems for the oxidative coloration of hair.

One aspect of this invention comprises a high aqueous-content dye lotion formulation for use in a two-part composition for oxidative dyeing of hair, the dye lotion formulation comprising:
- at least about 50% by weight water;
- a tinctorial effective amount of at least one primary dye intermediate and
- at least one coupler for the formation of an oxidative dye; and
- a conditioning effective amount of hydroxypropyl bisisostearamidopropyl dimonium chloride (HPBISAPDC) conditioner.

A further aspect of this invention comprises a two-part aqueous composition for coloring and providing conditioning to human hair, the two-part aqueous composition comprising:
(a) an aqueous lotion first part comprising: a tinctorially effective amount of at least one primary dye intermediate and at least one coupler for the formation of oxidation dyes, a conditioning effective amount of hydroxypropyl bisisostearamidopropyl dimonium chloride conditioner, and at least about 50% by weight water; and
(b) an aqueous developer second part comprising: an oxidizing effective amount of a peroxide oxidizer and at least about 70% by weight water.

A still further aspect of this invention comprises a kit containing a two-part aqueous composition comprising separate first and second containers:
(a) the first container containing an aqueous lotion first part comprising: a tinctorially effective amount of at least one primary dye intermediate and at least one coupler for the formation of oxidation dyes, a conditioning effective amount of hydroxypropyl bisisostearamidopropyldimonium chloride conditioner, and at least about 50% by weight water; and
(b) the second container containing an aqueous developer second part comprising: an oxidizing effective amount of a peroxide oxidizer, at least about 70% by weight water.

Yet another aspect of this invention comprises a method of coloring human hair which comprises contacting the hair with a mixture of a two-part aqueous composition, wherein the two part aqueous composition comprises:

(a) an aqueous lotion first part comprising: a tinctorially effective amount of at least one primary dye intermediate and at least one coupler for the formation of oxidation dyes, a conditioning effective amount of hydroxypropyl bisisostearamidopropyldimonium chloride conditioner, and at least about 50% by weight water; and (b) an aqueous developer second part comprising: an oxidizing effective amount of a peroxide oxidizer, at least about 70% by weight water; and maintaining said contact until the hair is permanently colored.

An even still further aspect of the invention comprises a method for oxidative coloring of hair with a two-part dyeing composition comprising a first dye base lotion formulation and a second developer formulation, wherein the improvement comprises using as the dye base lotion formulation a formulation comprising:

at least about 50% by weight water;

a tinctorial effective amount of at least one primary dye intermediate and at least one coupler for the formation of an oxidative dye; and a conditioning effective amount of hydroxypropyl bisisostearamidopropyl-dimonium chloride conditioner.

In the preferred embodiments of the present invention, the dye lotion and the developer composition, when mixed at the time of use, form a composite hair dye product composition for application to hair that has a suitably high viscosity, and most preferably is in the form of a gel.

DETAILED DESCRIPTION OF THE INVENTION

The components in the aqueous first part of the compositions of this invention, i.e., the lotion, include water, the oxidizable dye precursors, a conditioning effective amount of HPBISAPDC conditioning agent suitably present in the formulation as Shercoquat 21AP, and, optionally, an anionic, nonionic, amphoteric or cationic surfactant or mixtures thereof, an anionic or nonionic thickeneing polymer, and particularly a monomeric quaternary compound.

Unless otherwise specified the amounts of the various ingredients in the compositions of this invention are in percent by weight based on the total weight.

The water content of the composition is at least about 50% by weight and may be as high as 90% or higher and is preferably at least about 65% to about 85%.

The conditioning effective amount of the HPBISAPDC conditioning agent employed will generally be from about 0.1% to about 5% by weight, preferably about 1% to about 3%, and more preferably about 2%. It has been found, surprisingly, that HPBISAPDC provides excellent conditioning to hair while the hair is wet, before, during and after the final rinse of the hair to remove the hair dye product. The HPBISAPDC conditioning agent leaves the hair following the rinse step manageable and permits combing without tangling. This improved conditioning effect is believed to occur because the interaction of HPBISAPDC with anionic and amphoteric surfactants and polymers is to a lesser extent than with conventional monomeric quaternary compounds or polymer cationic compounds. This improvement in wet conditioning is very important to the consumer and hair colorist because the hair is more easily managed with less tangles, snarls and pulls, and feels softer and smoother, notwithstanding the treatment of the hair with the hair color products, including hydrogen peroxide that causes damage to the hair by its bleaching action.

The oxidative dye precursors employed in the practice of this invention comprise one or more primary intermediates together with one or more couplers. The selection of specific intermediates or couplers determines the ultimate color of the treated hair. Such selection is not a critical aspect of the practice of the invention.

A wide variety of primary intermediates can be employed in this invention is including, for example:

p-phenylenediamine derivatives such as: benzene-1,4-diamine, 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-aminophenyl)-(2-hydroxy-ethyl)-amino]-ethanol, (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine,2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)oxy]ethoxy}ethoxy)ethoxy]benzene-1,4-diamine;

p-aminophenol derivatives such as: 4-amino-phenol, 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)phenol, and 4-amino-2-fluoro-phenol;

o-aminophenol derivatives such as: 2-amino-phenol, 2,4-diaminophenol, 2-amino-5-methyl-phenol, 2-amino-3-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4 (1H)-one, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole-4,5-diamine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4] naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]4,6-dimethoxyphenyl}amino) ethanol, 3-(2,4-diaminophenoxy)-propane-1,2-diol, 2-[2-amino-4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2,N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine , 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine,and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one,and 1H-indol-6-ol, and 2-aminopyridin-3-ol.

The primary intermediate(s) and coupler(s) in the aqueous lotion of the invention will normally be employed in equimolar quantities, each at a concentration of about 0.0005% to about 5% by weight, preferably 0.005% to 2.5% by weight.

It may be desirable in certain cases to include non-oxidative or direct dyes as a part of the hair color formulation to achieve different color effects. Examples of such direct or non-oxidative dye include, but are not limited to Yellow/Orange dyes: Acid Orange 3, Disperse Orange 3, Disperse Black 9, HC Orange 1, HC Orange 2, HC Orange 3, HC Yellow 2, HC Yellow 4, HC Yellow 5, HC Yellow 6, HC Yellow 7, HC Yellow 9, HC Yellow 10, HC Yellow 11, HC Yellow 12, HC Yellow 13, HC Yellow 14, HC Yellow 15,4-nitro-o-phenylenediamine, 2-nitro-5-glyceryl methylaniline, 4-nitrophenyl aminoethylurea, hydroxyethyl-2-nitro-p-toluidine, 3-methylamino-4-nitrophenoxyethanol, 2-amino-6-chloro-4-nitrophenol, 2-chloro-6-ethylamino-4-nitrophenol, Basic Yellow 57, Solvent Orange 45, 4-nitro-m-phenylenediamine, Natural Orange 6, 2-hydroxyethylamino-5-nitroanisole, 2-amino-3-nitrophenol, 6-nitro-o-toluidine, N-ethyl-3-nitro PABA, N-hydroxyethyl-2,6-dinitro-p-anisidine, 6-nitro-2,5-pyridinediamine, and 4-chloro-5-methyl-2-nitrophenol;

Red-Orange/Red dyes: HC Red 1, HC Red 3, HC Red 7, HC Red 10, HC Red 11, HC Red 13, HC Red 14, 2-nitro-p-phenylenediamine, 3-nitro-p-hydroxyethylaminophenol, 4-hydroxypropylamino-3-nitrophenol, 4-amino-3-nitrophenol, picramic acid, N-(2-hyroxyethyl)picramic acid, Basic Red 76, Disperse Red 17, N-methyl-3-nitro-p-phenylenediamine, 2-chloro-5-nitro-N-hydroxyethyl-p-phenylenediamine, 4-amino-2-nitrodiphenylamine-2'-carboxylic acid, and 4-amino-4'-dimethylamino-2-nitrodiphenylamine-2'-carboxylic acid;

Violet dyes: Disperse Violet 1, Disperse Violet 4, HC Blue 2, HC Blue 6, HC Blue 9, HC Blue 10, HC Blue 11, HC Blue 12, HC Violet 1, HC Violet 2, N,N'-bis(2-hydroxyethyl)-2-nitro-p-phenylenediamine, 2-nitro-4-[bis(2-hydroxyethyl)amino]diphenylamine, and Basic Violet 14;

Blue dyes: Disperse Blue 1, Disperse Blue 3, Basic Blue 7, Basic Blue 9, Basic Blue 26, Basic Blue 17, Basic Blue 99, Disperse Blue 377, and Brown/Black dyes: Basic Brown 16, Basic Brown 17, and Acid Black 1.

The choice of these dyes for inclusion in a high aqueous-content dye lotion formulation of this invention will be based upon the stability of the resulting alkali lotion formulation when the dye is included.

Suitable conventional cosmetic additive ingredients useful in the hair dye i5 and developer compositions, and hence in the composite (i.e., admixed) hair dye product compositions of this invention are described below, and may be used to obtain desired characteristics of the hair dye, developer, and hair dye product compositions.

Anionic and nonionic surfactant compounds may be incorporated into the compositions of the present invention. Suitable surfactants include fatty alcohol sulfates, ethoxylated fatty alcohol sulfates, alkylsulfonates, alkylbenzensulfonates, ethoxylated fatty alcohols, ethoxylated fatty acids, ethoxylated alkylphenols, block polymers of ethylene and/orpropylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Useful anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1–3.

Amphoteric (including zwitterionic) surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group. There are a large number of amphoteric surfactants that are suitable for use in this invention. They include, for example, the asparagine derivatives identified in the first three patents mentioned above as well as a variety of well-known betaines, sultaines, glycinates and propionates that may be represented by the following structural formulas:

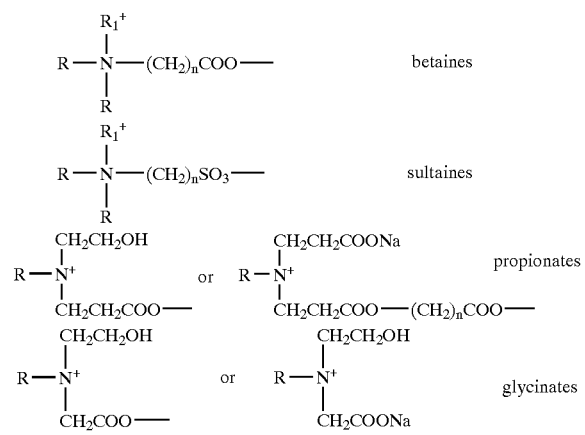

In the formulas, R is an alkyl or alkylamido group containing from about 10 to about 20 carbon atoms, R, $R_1$, $R_2$ and $R_3$ are alkyl or hydroxyalkyl groups, which may be the same or different, and contain up to about five carbon atoms and n is a positive integer up to about five.

Typical amphoteric surfactants that are suitable for use in this invention include: lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoampho-carboxypropionate, cocoamphocarboxyglycinate, coco-betaine, cocoamphopropionate, cocoamphopropylsulfonate. The amphoteric surfactants presently preferred for use in this invention are: cocamidopropyl betaine, coco-betaine, stearyl betaine, cocoamphocarboxyglycinate, cocoamphodipropionate, and stearoamphoglycinate.

The anionic, nonionic and amphoteric surfactants and mixtures of these surfactants for use in this invention are included for various reasons as known in the art, e.g., to assist in thickening, for forming emulsions, to impart foaming in shampoo-in tint products, to help in wetting hair during application of the hair dye product composition, etc., and may be selected from any of a number of known surfactants including those set forth above. The amount of such surfactants in the compositions is normally from about 0.5% to 15% by weight, preferably 2% to 8% by weight.

The pH of the lotions of this invention will generally be from about 6.5 to about 11. It is preferred, however, that this pH be in the range of 8.5 to 10.5.

Any of a wide variety of alkaline agents can be used to adjust the pH of the hair coloring compositions. Ammonium hydroxide, because of its freedom from toxicity over a wide concentration range and its economy, is an acceptable alkalizing agent. However, there can be used in place of, or together with, ammonium hydroxide any other compatible ammonia derivative as an alkalizing agent, such as an alkylamine, for example ethylamine, or triethylamine; or alkanolamines, for example ethanolamine, diethanolamine, aminomethyl propanol, aminomethyl propanediol and trishydroxymethyl aminomethane. Likewise, any other of the organic or inorganic alkalizing agents may be used, such as sodium or potassium hydroxide, sodium or potassium carbonate, sodium phosphate, sodium hydrogen phosphate, sodium silicate, guanidine hydroxide and the like. The preferred alkaline reagents are ammonium hydroxide, sodium carbonate and ethanolamine.

With the agents listed above, the selected pH will generally be achieved if the lotion contains from about 0.1% to 10% by weight of alkaline agent.

Monomeric quaternary compounds may be included in the dye lotion formulations of the present invention as co-conditioners along with HPBISAPDC. Because HPBISAPDC is incorporated, the conventional monomeric quaternary compounds can be reduced in concentration or altogether excluded. Thus, it is possible to substitute HPBISAPDC that has reduced interaction with anionic materials as compared to these conventional quaternary compounds.

Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12–18 dialkyldimonium chloride, cetalkonium chloride, ceteartrimonium bromide and chloride, cetrimonium bromide, chloride and methosulfate, cetylpyridonium chloride, cocamidoproypl ethyldimonium ethosulfate, cocamidopropyl ethosulfate, coco-ethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference.

The presently preferred cationic polymers are quaternary polymers of diallyidialkylammonium salts in which the alkyl groups are the same or different and contain from 1 to 5 carbon atoms such as Merquat 100 (Calgon) or copolymers of the above with acrylic acid sold under the names Merquat 280 and Merquat 295, such as those described in U.S. Pat. No. 4,772,462. Surprisingly, it has been observed that the copolymers of diallyidialkylammonium salts with acrylamide, such as that sold under the name Merquat 550, are unsuitable for this purpose. Also useful is the zwitterionic polymer Polyquaternium 47 sold by Nalco Company under the tradename Merquat 2001. Other useful polymers include Onamer M (Onyx) a polydimethylbutenyl chloride end-capped with hydroxyalykl groups of the formula:

where $R_3$ is a hydroxyalkyl group having 1–5 carbon atoms, preferably 2.

Quaternized polyvinylpyridine where R is alkyl or hydroxyalkyl having 1–5 carbon atoms and X is an anion such as chloride, bromide sulfate or alkylsulfate of the formula:

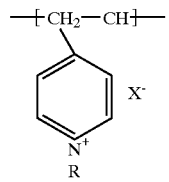

and polymethacrylamidopropyltrimethylammonium chloride

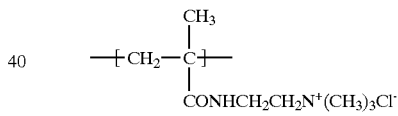

are also useful.

The cationic polymers may be incorporated in the hair dye lotion formulations and are useful conditioning agents for wet conditioning. The above mentioned polymeric materials are generally employed in the compositions of the present invention in an amount of from about 0.1% to about 5% by weight. As with the monomeric quaternary compounds, the cationic polymers are subject to interaction with anionic materials, which reduces their effectiveness. Accordingly, the HPBISAPDC conditioning agent can replace a portion or all of the cationic polymer.

The viscosity of the completely formulated dye lotion of the invention, when it is ready to mix with the developer, is from about 1 cps to about 5000 cps, preferably 1 cps to 500 cps.

The lotion may contain organic solvents to assist in dissolving the dye precursors. However, it has been observed that in the compositions of this invention, the organic solvent content should be kept at a minimum. More solvent than is necessary to dissolve the precursors may have the effect of retarding diffusion of the precursors into the hair for reaction. Accordingly, the organic solvent content of the lotion may be from 0% by weight to about 5% by weight.

Typically useful solvents include alcohols containing up to three carbon atoms such as ethanol and isopropanol, polyhydroxy alcohols such as propylene or hexylene glycol and lower alkyl ethers thereof such as ethoxy ethers.

Other conventional agents often employed in hair coloring compositions may be employed in the lotion or in the developer. These include, for example, fragrances, coloring agents and chelating agents. Antioxidants such as sodium sulfite, erythorbic acid, and ascorbic acid may also be included to inhibit premature oxidation.

The developer composition employed in the invention is an acidic aqueous composition, which comprises the selected oxidizing agent, and may include one or more anionic polymers or nonionic thickening polymers, as described below.

The preferred oxidizing agent for use in the developer of the invention is hydrogen peroxide although other peroxides may be employed. These include, for example, urea peroxide, melamine peroxide, perborates and percarbonates such as sodium perborate or percarbonate. The concentration of peroxide in the developer may be from about 0.5% to about 40% by weight, preferably 0.5% to 30% by weight. If the preferred hydrogen peroxide is employed, the concentration will be from about 0.5% to about 15% by weight, preferably 3% to 13% by weight.

An amphiphilic thickening polymer (i.e., a polymer having both hydrophilic and lipophilic groups) may be incorporated in the developer, which will provide thickening upon admixing of the acidic developer and the alkaline dye lotion. The thickening polymer should be stable to the peroxide oxidant, insoluble in the developer, and provide thickening when the developer is mixed with the dye lotion. The anionic polymer preferably employed in the developer solution is an acrylate/beheneth-25 methacrylate copolymer commercially available from Rohm and Haas, Philadelphia, Pa. under the name Aculyn® 28. Other anionic polymers, such as, for example, acrylates copolymer, a copolymer of acrylic or methacrylic acid with their lower alkyl esters (Aculyn® 33) or acrylates/steareth-20 methacrylate copolymer (Aculyn 22). Nonionic polymeric thickeners are PEG-150/stearyl/SMDI copolymer sold as Aculyn 44 and Aculyn 46 by Rohm & Haas. The composite composition containing the polymeric thickeners in the acidic developer composition is thickened in view of a change in the pH when mixed with the dye lotion, and/or when mixed with a dye lotion containing an associative agent such as a surfactant. Other nonionic amphiphilic polymer thickening agents are identified in U.S. Pat. No. 6,010,155, incorporated by reference. Other thickening methods are also useful, in particular the use of surfactant systems as mentioned above.

The concentration of anionic or nonionic polymer in the developer is from about 0.1% by weight to about 6% by weight, preferably about 0.5% to 4% by weight, most preferably about 1% to 3%, generally about 1.5% by weight. The developer solution will generally contain at least 70% by weight of water, preferably about 75 to 95% or more water.

The developer and/or the lotion may also contain from 0 to about 0.2% by weight of a stabilizer such as phenacetin or ethylene diamine tetracetic acid (EDTA); from about 0 to 0.10%, preferably about 0.001% to 0.01% by weight of an antifoam agent such as simethicone; from about 0 to about 2%, preferably about 0.1% to 0.5% by weight pH buffer, such as for example edidronic acid; and from 0 to about 5%, preferably about 1.5% to 3% of any suitable conditioners, emulsifiers and/or surfactants, particularly conditioners, emulsifiers and surfactants such as PEG-50 tallow amide conditioner, Oleth-2, Oleth-5, Oleth-10 and oleyl alcohol emulsifiers, and $C_{12}$–$C_{15}$ Pareth-3.

The viscosity of the developer as prepared for mixture with the lotion is from about 1 cps to about 5000 cps by weight, preferably 1 cps to 500 cps by weight.

It is desirable but not essential that the viscosities of the lotion and the developer be close to each other. If the difference in viscosities is too great they will be difficult to mix. On shaking the thinner solution will agitate well, but the thicker component will be more difficult to agitate and the rate of blending will be slowed down. One of the significant advantages of the composite hair dye product composition of this invention is its ability to sheer down (sheer down due to thinning) when the developer solution is dispensed from a squeezable bottle. However, the mixture then recovers its viscosity once applied to provide a non-drip product attribute that is require for a cosmetically acceptable hair dye product. Although gels are preferable, the composite hair dye product compositions may also be in the form of creams, thickened lotions or thickened solutions.

The pH of the developer is from about 2 to about 6, preferably 2.5 to 4.5, most preferably 2 to 3. Any of a variety of non-toxic acids or buffers may be employed to maintain pH. Etidronic acid and phosphoric acid are the most preferred.

The dye lotion of this invention can be prepared in the following manner:

Water is heated to about 50° C. to about 60° C. and the buffering agent added. Combine in a premix the conditioner and all emulsifiers and surfactants, and heat the premix to about 78° C. to about 80° C. Slowly add the heated premix to the heated buffered water solution and mix for approximately 20 minutes until a substantially uniform solution is obtained. Cool the solution with DI water and add the primary intermediate(s) and coupler(s), to the solution at a temperature below about 40° C. Then individually add the thickeners and antifoam agents to the solution and mix the resulting solution until essentially uniform.

The developer composition is made by admixing of the oxidant, water and other ingredients in a suitable mixing vessel with agitation. Water is heated to 80–85° C. Oil soluble components are mixed and premelted to 80° C. This mixture is added to the water slowly with agitation. Other materials are then added to the solution. The mixture is cooled and polymeric thickeners, hydrogen peroxide and an acid component are added, and the entire mixture is then cooled to room temperature while mixing.

To use the product of the present invention, which may be in the form of a kit, the lotion and developer are mixed just before application to the hair to form the composite hair dye product composition. On mixing and accordingly when in contact with the hair, a stable gel (or other thickened composite composition such as a cream or thickened lotion) with enough consistency and body and a viscosity of about 6,000 to about 30,0000 cps to remain on the hair during the complete coloring period without dripping or running is formed. Preferably, the resulting mixture exhibits the ability to "sheer down" during mixing to allow the developer/polymer solution to intermingle easily with the dye base components in the lotion when mixed, during which time the polymer is neutralized with a portion of the alkali, already present in the lotion composition, and thickening occurs. The primary intermediate and coupler, i.e., the dye precursors, diffuse rapidly into the hair together with the oxidizing agent. The dyes form within the hair fiber and, since they are large molecules, remain in the hair so that the color change is permanent. The term "permanent" means that the dye does not readily wash out of the hair with ordinary shampoos. The color achieved with the products of this invention is so stable that it may survive as many as 20 shampoos without noticeable change.

Moreover, the use of the Schercoquat 21AP conditioner results in improved color uptake compared to previously used conditioners and permits a reduction in the total amount of active dye ingredients employed in the compositions as demonstrated in the Examples appearing hereinafter. The use of Schercoquat 21AP conditioning agent in the lotion formulation of the two-part hair dyeing compositions of this invention provides excellent wet feel and wet combing characteristics immediately after the dyeing mixture is rinsed from the dyed hair. Additionally, the chemical nature of Schercoquat 21AP is such that the conditioning benefits provided do not interfere with the conditioning benefits provided by other ancillary products typically applied post-coloring, such as after-color conditioners or treatments. The compositions of this invention produce a hair dye system that has excellent stay-put and application properties, and provide the opportunity to more efficiently deliver conditioning materials resulting in improved product performance.

At the end of the coloring period, the composition is washed from the hair with an ordinary water rinse followed by a shampoo.

The compositions of this invention may be separately provided in a kit or package form ready for mixing by the user, either professional or personal, to initiate the dyeing process. It is preferred to mix them in a mixing vessel for subsequent application to the hair as the gel forms.

The kit provided in accordance with this invention comprises those containers. In the most convenient form, there will be two containers, one containing the lotion, the other the developer, and written instructions. Particularly when a solid oxidant is employed, it may be convenient to package the developer in separate containers one with the oxidizing agent, the other with the anionic polymer in water. With both embodiments of the invention, the ingredients in the aqueous composition of the first container will include the dye precursors and the Schercoquat 21AP conditioning agent.

The method of the invention comprises applying the dyeing mixture containing the Schercoquat 21AP conditioning agent to the hair to be colored and allowing it to remain in contact with the hair until the desired hair color has been attained after which the composition is removed from the hair as described above.

The following non-limiting example is given by way of illustration only.

EXAMPLE

Dye Base Lotions of this Invention (Formulations A, B, C and D) were Prepared from the Following Ingredients

| Ingredient | Wt. % |
|---|---|
| FORMULATION A | |
| D.I. water | 58.8420 |
| Hexylene glycol | 15.6000 |
| C11–15 Pareth-9 | 4.5300 |
| Monoethanolamine | 4.5000 |
| Dilinoleic acid | 3.6000 |
| Soytrimonium chloride and propylene glycol | 3.4000 |
| Schercoquat 21AP | 2.0000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |
| Sodium sulfite | 0.1000 |
| Cyclomethicone | 0.0100 |
| FORMULATION B | |
| D.I. water | 58.8420 |
| Hexylene glycol | 15.6000 |
| C11–15 Pareth-9 | 4.5300 |
| Aminomethylpropanol | 3.0000 |
| Dilinoleic acid | 3.6000 |
| Soytrimonium chloride and propylene glycol | 3.4000 |
| Schercoquat 21AP | 2.0000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |
| Sodium sulfite | 0.1000 |
| Cyclomethicone | 0.0100 |
| FORMULATION C | |
| D.I. water | 58.8420 |
| Hexylene glycol | 15.6000 |
| C11–15 Pareth-9 | 4.5300 |
| Ammonium hydroxide | 6.0000 |
| Dilinoleic acid | 3.6000 |
| Soytrimonium chloride and propylene glycol | 3.4000 |
| Schercoquat 21AP | 2.0000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |
| Sodium sulfite | 0.1000 |
| Cyclomethicone | 0.0100 |
| FORMULATION D | |
| D.I. water | 58.8420 |
| Hexylene glycol | 15.6000 |
| C11–15 Pareth-9 | 4.5300 |
| Monoethanolamine | 3.0000 |
| Ammonium hydroxide | 3.0000 |
| Dilinoleic acid | 3.6000 |
| Soytrimonium chloride and propylene glycol | 3.4000 |
| Schercoquat 21AP | 2.0000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |

-continued

| Ingredient | Wt. % |
|---|---|
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |
| Sodium sulfite | 0.1000 |
| Cyclomethicone | 0.0100 |

A further base lotion formulation of this invention (Formulation E) was similarly formulated from the same ingredients as follows:

FORMULATION E

| Ingredient | Wt. % |
|---|---|
| D.I. water | 56.4420 |
| Hexylene glycol | 15.6000 |
| C11–15 Pareth-9 | 4.5300 |
| Monoethanolamine | 4.5000 |
| Dilinoleic acid | 3.6000 |
| Soytrimonium chloride and propylene glycol | 6.8000 |
| Schercoquat 21AP | 2.0000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |
| Sodium sulfite | 0.1000 |
| Cyclomethicone | 0.0100 |

For comparison purposes a similar lotion formulation (Formulation F), without the Schercoquat 21AP conditioner of this invention present, was prepared from the same ingredients as follows:

FORMULATION F

| Ingredient | Wt. % |
|---|---|
| D.I. water | 58.4420 |
| Hexylene glycol | 15.6000 |
| C11–15 Pareth-9 | 4.5300 |
| Monoethanolamine | 4.5000 |
| Dilinoleic acid | 3.6000 |
| Soytrimonium chloride and propylene glycol | 6.8000 |
| Oleamide MIPA | 1.5000 |
| Fragrance | 1.0000 |
| p-Aminophenol | 0.6870 |
| Oleth-10 | 0.6800 |
| Erythorbic acid | 0.5000 |
| Citric acid | 0.5000 |
| Resorcinol | 0.4950 |
| m-Aminophenol | 0.3820 |
| p-Phenylenediamine | 0.2920 |
| 1-Naphthol | 0.1820 |
| EDTA | 0.1000 |
| Oleth-2 | 0.1000 |

-continued

FORMULATION F

| Ingredient | Wt. % |
|---|---|
| Sodium sulfite | 0.1000 |
| Cyclomethicone | 0.0100 |

As examples of developer solutions useful with the dye lotion formulation of this invention there may be mentioned developer solutions G and H prepared from the following ingredients:

| Ingredient | Solution G Wt % | Solution H Wt % |
|---|---|---|
| D.I. water | 82.9740 | 82.9740 |
| Disodium EDTA | 0.0400 | 0.0400 |
| Etidronic acid | 0.0800 | 0.8000 |
| PEG-50 tallow amine | 1.0000 | 1.0000 |
| Oleth-2 | 1.0000 | 1.0000 |
| Oleth-5 | 1.0000 | 1.0000 |
| Oleyl alcohol | 0.3000 | 0.3000 |
| Stereth-21 | 2.0000 | 2.0000 |
| Hydrogen peroxide | 5.6000 | 2.0000 |
| Aculyn ®-28 | 6.0000 | — |
| Simethicone | 0.6000 | 0.6000 |

Developer solution G was mixed with each of the three lotions Formulation A, E, and F and each of the resulting mixtures were each applied to bleached hair, piedmont hair and gray hair and color uptake measurements taken on a colorimeter. The shade used was a medium neutral blonde (7N). The Minolta 3700d spectrophotometer employed for the measurements uses reflected light from a surface and gives results in terms of the CIE (International Commission on Illumination) tristimulus values. These values are subsequently transformed mathematically into the L*a*b* color space, wherein the magnitude of changes in hue and intensity of color correspond closely with those perceived by the human eye. L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y-axis to give quantitative color information: "metric chroma" is the length of a line from the origin (a*=0, b*=0) to the point of a sample reading while metric hue angle is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The readings for Formulation F were taken as the baseline and the readings for Formulations A and E were compared thereto to determine the ΔE as indicative of the color uptake efficacy of the Schercoquat 21AP conditioner. ΔE is defined by the following formula:

$$\Delta E = \sqrt{(L^*_f - L^*_i)^2 + (a^*_f - a^*_i)^2 + (b^*_f - b^*_i)^2}$$

where e $L^*_f$, $a^*_f$ and $b^*_f$ are the values for the formulation of this invention and $L^*_i$, $a^*_i$ and $b^*_i$ are the baseline values for Formulation F.

The results of the measurements and ΔE calculation were as follows:

| Formulation | L* | a* | b* | ΔE |
|---|---|---|---|---|
| | 7N bleached hair | | | |
| A | 17.56 | 1.75 | 1.41 | 2.34 |
| E | 17.29 | 1.81 | 1.74 | 2.39 |
| F | 19.41 | 2.32 | 2.72 | |
| | 7N piedmont hair | | | |
| A | 29.20 | 6.05 | 13.53 | 3.48 |
| E | 41.66 | 5.88 | 14.42 | 0.89 |
| F | 19.41 | 2.32 | 2.72 | |
| | 7N gray hair | | | |
| A | 28.68 | 3.02 | 6.47 | 1.36 |
| E | 26.88 | 2.97 | 6.08 | 2.67 |
| F | 28.91 | 3.24 | 7.79 | |

Conditioning, visual coloration and viscosity results were also evaluated for the three formulations and the following results were observed.

| Conditioning results | Formulation A | Formulation E | Formulation F |
|---|---|---|---|
| Wet stage (feel and comb) | Better | Best | Good |
| Color result | Slightly Intense | More intense | Less intense |
| Mixed viscosity (cps) | 13,104 | 31,200 | 15,600 |

The results indicate that the Shercoquat 21AP conditioner can provide improved conditions effects without inhibiting the dyeing effect and also indicates that the same or improved results can be obtained with less active ingredients. For example, Formulation A is able to obtain improved results over Formulation F even though the amount of soytrimonium chloride has been reduced from 6.8% to 3.4% and the total amount of Schercoquat 21AP and soytrimonium chloride is only 5.4%. Formulation E compared to Formulation F shows that the use of Shercoquat 21AP along with the soytrimonium chloride synergistically improves the performance of a formulation containing the soytrimonium chloride conditioner.

Illustrative of typical lotion formulations of this invention containing dye components and Shercoquat 21AP conditioner are those which may have the following exemplary components in the indicated amounts, although it will be recognized that this is merely an exemplary formulation and formulation with other components are within the scope and spirit of this invention.

Typical Lotion Formulations of This Invention Containing Dye Components and Shercoquat 21AP Conditioner

| Ingredient | Function | General Range (%) | Preferred Range (%) |
|---|---|---|---|
| Water | solvent | 50–90 | 65–80 |
| Propylene glycol | solvent | 0–10 | 2–5 |
| C11–C15 Pareth-9 | surfactant | 0–6 | 2–3 |
| C12–C15 pareth-3 | surfactant | 0–5 | 2–3 |
| Ethanolamine | alkalinity agent | 0–15 | 3–6 |
| Oleth-10 | emulsifier | 0–8 | 1–3 |
| Oleth-2 | emulsifier | 0–8 | 1–3 |
| Sodium sulfite | antioxidant | 0.1–1 | 0.1–0.5 |
| Erythorbic acid | antioxidant | 0.1–1 | 0.1–0.5 |
| EDTA | chelating agent | 0.01–0.5 | 0.05–0.2 |
| Cyclomethicone | antifoam | 0.01–0.2 | 0.01–0.05 |
| Citric acid | buffer | 0–0.2 | 0.01–0.05 |
| Ammonium hydroxide (28%) | alkalinity agent | 0–17 | 0.2–0.7 |
| Steareth-21 | emulsifier | 3–6 | 1–3 |
| Lauryl alcohol | emulsifier | 3–6 | 1–3 |
| Laureth-23 | emulsifier | 3–7 | 1–3 |
| Ceteralyl alcohol | emulsifier | 4–7 | 1–3 |
| Dilinoleic acid | fatty acid | 1–10 | 3–35 |
| p-Phenylenediamine | dye | 0–5 | 0.05–2 |
| Resorcinol | dye | 0–5 | 1–3 |
| Mica | pearling agent | 0–2 | 0.1–1 |
| Hexylene glycol | solvent | 0–20 | 0.3–8 |
| Ethoxydiglycol | solvent | 0–10 | 2–5 |
| Cocamidopropyl betaine | surfactant | 0–5 | 1–3 |
| PEG-150/stearyl/SMDI copolymer | thickener | 0–5 | 1–3 |
| Oleamide MIPA | co-emulsifier | 0–4 | 1–2 |
| Soytrimonium chloride/propylene glycol | conditioner | 0–7 | 2–4 |
| Schercoquat 21AP | conditioner | 0.1–5 | 1–3 |
| Behetrimonium chloride | conditioner | 0–6 | 1–3 |
| Polyquaternium-22 | conditioner | 3–7 | 3–7 |
| Linoleamidopropyl dimethylamine | conditioner | 0–6 | 1–3 |

Each solution, i.e., dyeing lotion formulation and developer solution formulation is packaged in a separate container for use as a dyeing kit. Upon discharge of the developer solution from a squeezable container and mixing with the dye base lotion, a desired thickening occurs to provide a non-drip dyeing product with excellent conditioning properties.

With the foregoing description of the invention, those skilled in the art will appreciate that modification may be made to the invention without departing from the spirit thereof. Therefore, it is not intended that the scope of the invention be limited to the specific embodiments illustrated and described.

What is claimed is:

1. A high aqueous-content dye lotion formulation for use in a two-part composition for oxidative dyeing of hair, the dye lotion formulation comprising:
   at least about 50% by weight water;
   a tinctorial effective amount of at least one primary dye intermediate and at least one coupler for the formation of an oxidative dye; and
   a conditioning effective amount of hydroxypropyl bisisostearamidopropyldimonium chloride conditioner.

2. The dye lotion formulation of claim 1 wherein the conditioner is present in the lotion formulation in an amount of from about 0.1 to about 3% by weight.

3. The dye lotion formulation of claim 1 wherein the conditioner is present in the lotion formulation in an amount of from about 1 to 3% by weight.

4. A two-part aqueous composition for coloring and providing conditioning to human hair, the two-part aqueous composition being adapted for admixture to form a hair dye product composition and comprising:
   (a) an aqueous dye lotion first part comprising: a tinctorially effective amount of at least one primary dye intermediate and at least one coupler for the formation of oxidation dyes, a conditioning effective amount of hydroxypropyl bisisostearamidopropyldimonium chloride conditioner, and at least about 50% by weight water; and (b) an aqueous developer second part comprising: an oxidizing effective amount of a peroxide oxidizer and at least about 70% by weight water.

5. The two-part aqueous composition of claim 4 wherein (a) the aqueous lotion first part has a pH of from about 7 to about 11 and contains from about 0.005% by weight to about 5% by weight of each of the at least one primary dye intermediate and the at least one coupler for the formation of oxidation dyes, a conditioning effective amount of at least about 0.1% by weight of the hydroxypropyl bisisostearamidopropyldimonium chloride conditioner; and (b) the aqueous developer second part has a pH of from about 2 to about 6 and contains from about 0.5% by weight to about 30% by weight of the peroxide oxidizer.

6. The composition of claim 5 wherein the dye lotion further comprises at least one surfactant selected from the group consisting of anionic, nonionic and amphoteric surfactants in an amount effective to thicken the hair dye product composition when the dye lotion and developer are mixed.

7. The composition of claim 5 wherein the developer further comprises an amphiphilic polymer selected from the group consisting of anionic and nonionic polymers in an amount effective to thicken the hair dye product composition when the dye lotion and developer are mixed.

8. The composition of claim 6 wherein:
a: the pH of the lotion is from 9.0 to 10.5, each of the primary dye intermediate and the coupler is from 0.005% to 2.5% by weight; and
b: the pH of the aqueous developer is from 2.5 to 4.5, the peroxide oxidizer content is from 0.5% to 15% by weight hydrogen peroxide, and the water content is from about 70% to about 95% by weight.

9. The composition of claim 7 wherein:
a: the pH of the lotion is from 9.0 to 10.5, each of the primary dye intermediate and the coupler is from 0.005% to 2.5% by weight; and
b: the pH of the aqueous developer is from 2.5 to 4.5, the peroxide oxidizer content is from 0.5% to 15% by weight hydrogen peroxide, and the water content is from about 70% to about 95% by weight.

10. The composition of claim 8 wherein the developer contains from about 3% to about 13% by weight of hydrogen peroxide.

11. The composition of claim 9 wherein the developer contains from about 3% to about 13% by weight of hydrogen peroxide.

12. The composition of claim 4 wherein the aqueous dye lotion first part additionally comprises a monomeric quaternary surfactant.

13. The composition of claim 5 wherein:
the primary dye intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and
the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

14. A kit containing a two-part aqueous composition of the type adapted for mixture of the two parts to form a hair dye product composition comprising separate first and second containers:

(a) the first container containing an aqueous lotion first part comprising: a tinctorially effective amount of at least one primary dye intermediate and at least one coupler for the formation of oxidation dyes, a conditioning effective amount of hydroxypropyl bisisostearamidopropyldimonium chloride conditioner, and at least about 50% by weight water; and (b) the second container containing an aqueous developer second part comprising: an oxidizing effective amount of a peroxide oxidizer and at least about 70% by weight water.

15. The kit according to claim 14 wherein:

(a) the first container containing the aqueous lotion first part has a pH of from about 7 to about 11 and contains from about 0.005% to about 5% by weight of each of the at least one primary dye intermediate and the at least one coupler for the formation of oxidation dyes, a conditioning effective amount of at least about 0.1% by weight of the hydroxypropyl bisisostearamidopropyldimonium chloride conditioner; and (b) the second container containing the aqueous developer second part has a pH of from about 2 to about 6 and contains from about 0.5% to about 30% by weight of the peroxide oxidizer.

16. The kit of claim 15 wherein:
a: the pH of the lotion is from 9.0 to 10.5, each of the primary dye intermediate and the coupler is from 0.005% to 2.5% by weight, and the content of the conditioner is from about 1% to about 3% by weight; and
b: the pH of the aqueous developer is from 2.5 to 4.5, the peroxide oxidizer content is from 0.5% to 15% by weight hydrogen peroxide, and the water content is about 70% to about 95% by weight.

17. The kit of claim 16 further comprising a thickening agent, wherein the thickening agent is at least one of:

(a) at least one surfactant present in the dye lotion, said surfactant being selected from the group consisting of anionic and nonionic surfactants; and (b) an amphiphilic polymer present in the developer composition, said polymer being selected from the groups of anionic and nonionic polymers, said thickening agent being present in an amount effective to thicken the mixture of the dye lotion and the developer.

18. The kit of claim 15 wherein the developer contains from about 0.5% to about 15% by weight of hydrogen peroxide.

19. The kit of claim 17 wherein the developer contains from about 3% to about 13% by weight of hydrogen peroxide.

20. The kit of claim 14 wherein the aqueous liquid lotion first part in the first container additionally comprises a monomeric quaternary surfactant.

21. The kit of claim 16 wherein:

the primary dye intermediate is selected from the group consisting of the primary intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

22. A method of coloring human hair which comprises (A) contacting the hair with a mixture of a two-part aqueous composition wherein the two part aqueous composition comprises:
  (a) an aqueous lotion first part comprising: a tinctorially effective amount of at least one primary dye intermediate and at least one coupler for the formation of oxidation dyes, a conditioning effective amount of hydroxypropyl bisisostearamidopropyldimonium chloride conditioner, and at least about 50% by weight water; and
  (b) an aqueous developer second part comprising: an oxidizing effective amount of a peroxide oxidizer and at least about 70% by weight water;

(B) maintaining such contact until the hair is permanently dyed, and (C) removing the mixture from the hair.

23. The method of claim 22 wherein:
  (a) the aqueous lotion first part has a pH of from about 7 to about 11 and contains from about 0.005% to about 5% by weight of each of the at least one primary dye intermediate and at the least one coupler for the formation of oxidation dyes, and a conditioning effective amount of at least about 0.15 by weight of the hydroxypropyl bisisostearamidopropyldimonium chloride conditioner; and
  (b) the aqueous developer second part has a pH of from about 2 to about 6 and contains from about 0.5% to about 30% by weight of the peroxide oxidizer.

24. The method of claim 23 wherein:
  (a) with regard to the aqueous lotion, the pH of the lotion is from 9.0 to 10.5, the primary dye intermediate content is from 0.005% to 2.5% by weight, the coupler content is from 0.005% to 2.5% by weight, the hydroxypropyl bisisostearamidopropyldimonium chloride conditioner content is from about 0.1 to about 5% by weight; and
  (b) with regard to the developer composition, the pH of the aqueous developer is from 2.5 to 4.5, and the peroxide oxidizer content is from 0.5% to 15% by weight.

25. The method of claim 23 wherein the developer contains from about 0.5% to about 15% by weight of hydrogen peroxide.

26. The method of claim 25 wherein the developer contains from about 3% to about 13% by weight of hydrogen peroxide.

27. The method of claim 22 wherein the aqueous lotion first part additionally comprises a monomeric quaternary surfactant.

28. The method of claim 24 wherein:

the primary dye intermediate is selected from the group consisting of the primary intermediate is selected from the group consisting of 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol. 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol; and the coupler is selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

29. The method of claim 25 wherein the two-part aqueous composition further comprises a thickening agent, wherein the thickening agent is at least one of:
  (a) at least one surfactant present in the dye lotion, the surfactant being selected from the group consisting of anionic and nonionic surfactants; and
  (b) an amphiphilic polymer present in the developer composition, the polymer being selected from the groups of anionic and nonionic polymers, said thickening agent being present in an amount effective to thicken the mixture of the dye lotion and the developer.

* * * * *